(12) United States Patent
Möller et al.

(10) Patent No.: US 7,419,540 B2
(45) Date of Patent: Sep. 2, 2008

(54) SWELLABLE PHYLLOSILICATES

(75) Inventors: Markus Möller, München (DE); Helmut Coutelle, Freising (DE); Robert Warth, Moosburg (DE); Wolfgang Heininger, Moosburg (DE)

(73) Assignee: Sud-Chemie AG, Munich (DE)

( * ) Notice: Subject to any disclaimer, the term of this patent is extended or adjusted under 35 U.S.C. 154(b) by 658 days.

(21) Appl. No.: 10/362,305

(22) PCT Filed: Aug. 29, 2001

(86) PCT No.: PCT/EP01/09951

§ 371 (c)(1), (2), (4) Date: May 21, 2003

(87) PCT Pub. No.: WO02/18292

PCT Pub. Date: Mar. 7, 2002

(65) Prior Publication Data

US 2004/0037894 A1  Feb. 26, 2004

(30) Foreign Application Priority Data

Aug. 29, 2000  (DE) ................ 100 42 455

(51) Int. Cl.
*C04B 14/04* (2006.01)
(52) U.S. Cl. .............. 106/487; 106/486; 106/811; 106/718; 106/716; 510/515; 501/79; 501/147
(58) Field of Classification Search ......... 106/486–487, 106/811, 718, 716; 510/515; 501/79, 179, 501/147; 424/684
See application file for complete search history.

(56) References Cited

U.S. PATENT DOCUMENTS

| | | | | |
|---|---|---|---|---|
| 2,036,617 A | | 4/1936 | Bechtner et al. | |
| 3,343,973 A | * | 9/1967 | Billue | .......... 428/452 |
| 3,822,827 A | * | 7/1974 | Clark | ............ 241/3 |
| 4,351,754 A | * | 9/1982 | Dupre | ........... 524/445 |
| 5,266,538 A | | 11/1993 | Knudson et al. | |
| 5,389,146 A | * | 2/1995 | Liao | ............ 106/811 |
| 5,407,480 A | | 4/1995 | Payton et al. | |
| 5,480,578 A | | 1/1996 | Hirsch et al. | |
| 5,588,990 A | | 12/1996 | Dongell | |
| 5,637,144 A | | 6/1997 | Whatcott et al. | |
| 5,948,156 A | * | 9/1999 | Coutelle et al. | ............ 106/486 |

FOREIGN PATENT DOCUMENTS

| | | |
|---|---|---|
| CH | 459858 | 7/1968 |
| DE | 219170 | 2/1985 |
| DE | 4217779 | 12/1993 |
| DE | 4413672 | 10/1995 |
| DE | 4438305 | 5/1996 |
| DE | 19527161 | 1/1997 |
| EP | 409974 | 1/1991 |
| EP | 675089 | 10/1995 |

OTHER PUBLICATIONS

Bjorn Lagerblad and Berit Jacobson, "Proc. Int. Conf. Cem. Microsc." (1997) (19th Edition, pp. 151-162).
"Applied Clay Science," I(1986) pp. 273-284.

* cited by examiner

*Primary Examiner*—Jerry Lorengo
*Assistant Examiner*—Pegah Parvini
(74) *Attorney, Agent, or Firm*—Scott R. Cox

(57) ABSTRACT

A swellable layer silicate is described based on smectite or sepiolite/palygorskite for use in media containing di- or polyvalent cations that reduce swellability, characterized by a swelling volume of about 5 to 50 mL, measured by addition of 2 g layer silicate (air-dried) to 100 mL water, and by a fineness of maximum 5 wt. % >40 μm and maximum 20% >20 μm, as dry sieve residue.

13 Claims, No Drawings

SWELLABLE PHYLLOSILICATES

The invention concerns improved swellable layer silicates based on smectite for use in media that reduce swellability.

The use of swellable layer silicates based on smectite, for example, bentonites, montmorillonites, hectorites, etc., for example, in mineral binder systems, in paints and/or lacquers, cosmetics, lubricating greases and a number of other applications, is known.

It is generally noted here that the layer silicates usable for this purpose must satisfy certain requirements that depend on the corresponding application. For example, no negative phenomena should occur in cement systems, like cracking or shrinkage. It is pointed out by Björn Lagerblad and Berit Jacobson in "Proc. Int. Conf. Cem. Microsc." (1997) (19$^{th}$ Edition, pages 151-162) that the use of swellable smectites in cement and/or concrete leads to problems with cracking.

A possibility of overcoming this problem is described in EP-A 0 675 089, wherein the swellable layer silicates can be used in cement mineral binder systems. The auxiliary described in this document for mineral binder systems consists of at least 60% swellable layer silicates with a swelling volume of about 5 to 50 mL, referred to a suspension of 2 g layer silicate in 100 mL water. The fineness of the layer silicate is not explicitly mentioned: however, on page 3, line 32, a "typical" maximum sieve residue of about 20 wt. % 90 μm is mentioned. A significant teaching of this document is that bentonites represent an appropriate compromise with a special swelling volume in which a certain plasticization still occurs, on the one hand, but where there is no hazard that the set systems will exhibit shrinkage cracks, on the other.

In many other dry mortar systems that are also used in the construction industry, the swelling capacity of smectitic layer silicates, however, is not a limiting factor. Swellable layer silicates are generally not employed in these systems based on gypsum or lime/gypsum combinations, because the "potential" effect of these materials does not offer an appropriate advantage.

Alther, in "Applied Clay Science", I (1986) pages 273 to 284, clearly states that the presence of gypsum even in small amounts adversely affects the rheological properties of bentonites.

This "potential" effect on products is based, on the one hand, on the pronounced layer structure, and, on the other hand, on the swellability in water and the related high surface. Because of the layer structure, layer silicates can act as an internal lubricant as soon as the lamellae are separated from each other on entry of water and can slide over each other. Because of this, the normally highly filled systems become much more pliable and are easier to pump. A number of applications are improved by this, like pumpability of the ready-to-use systems, manual application of otherwise viscous systems, like tile adhesives, wall mortars, "casting" of plaster or application of finishing plaster, reduction of sedimentation of coarse additives in flowable systems (flow coats and filling mortars), etc.

This potential effect of swellable layer silicates, however, can only be utilized with restrictions, since, because of their nature, use in systems that contain larger amounts of soluble cations, especially divalent cations, like Ca ions, is limited. The commonly used layer silicates, like bentonites, montmorillonites, hectorites, etc. are colloidal systems that contain monovalent cations between the lamellae. Only when their hydration energy is higher than the attraction of negatively charged lamellae by these cations do these materials swell in the presence of water. Smectites with sodium ions between the layers are therefore particularly suitable. Owing to the charge density of the other alkali ions, Li- or K-smectites are already much less swellable than the corresponding Na-smectites.

When divalent cations are added and/or are present, however, these materials generally flocculate very quickly, since only conditionally and internally "swelling" layer silicates are formed from the swellable layer silicates by ion exchange.

If, for reasons of simple handling, powdered and swellable layer silicates are used in a powder mixture that contains hydraulic or latent-hydraulic binders as essential components that liberate relatively large amounts of divalent Ca ions in the presence of water, a competitive reaction occurs between water incorporation between the layer silicate lamellae (swelling) and the opposing flocculation. When a layer silicate powder is mixed into a powdered binder system that is also rich in water-soluble Ca ions, the layer silicate is hampered from swelling from the outset during addition of water to the powder mixture, so that the potential effect does not come into play from the very start.

The efficiency of the products therefore normally corresponds only to a fraction of their "theoretical" effect, since part of the effect is nullified by incorporation of divalent cations and "flocculation" in the presence of Ca ions. The swellable layer silicate is therefore ordinarily used in the form of a pre-dispersed suspension, since then it is at least ensured that the material is already fully swollen and a limitation of the effectiveness only occurs by subsequent flocculation.

However, this "two-component" method of operation is awkward and cannot be performed in all cases, since well swollen layer silicates that are supposed to be pumpable, in order to facilitate metering, can only be produced in a solids concentration of about 5 to 15 wt. %. In many areas of application, however, the addition of larger amounts of water, as introduced by suspensions or pastes with such low solids content, is not acceptable. Efforts were therefore made to furnish corresponding suspensions, in which the solids content can be raised to at least >20 wt. % (while retaining good pumpability) by adding wetting and/or dispersing auxiliaries to the smectite suspension, in order to get around this drawback.

WO 92/11218 describes a method of furnishing bentonite suspensions in highly concentrated form. The objective is to prepare stable suspensions with low viscosity. According to this document, readily pumpable suspensions with up to 50 wt. % swellable smectite can be produced by incorporating the swellable layer silicate not in water, but in a 3 to 15% NaCl solution. On dilution with water, the usual properties of the bentonite come into play.

A similar subject is described in WO 95/09135. Here again, the production of highly concentrated bentonite suspensions is involved, which can be achieved by means of amine salts of amines with low molecular weight. It is stated (page 4, lines 8 to 11) that all polyvalent cations have a tendency to bind the clay lamellae firmly to each other, which adversely affects dispersal. This clearly demonstrates that the use of bentonite in a medium containing polyvalent cations is at least doubtful. This is also considered to apply in systems, which, incorporated in water as powders, also produce high salt concentrations.

Although there is a possibility of using the corresponding layer silicates in critical systems, this method has some serious drawbacks:

The layer silicates must be processed separately, which is awkward and entails additional costs and requires additional machines.

The pasty or aqueous systems naturally cannot be incorporated in powder mixtures.

The semi-finished products (suspensions) contain additional salts that are not always desired and/or suitable in the system (ecological compatibility, blooming tendency, etc.).

The layer silicate dispersions so produced yield the desired properties only after further dilution with water, which is not possible, at least in the cement systems or those based on gypsum.

A similar subject is described in U.S. Pat. No. 5,389,146. In order to avoid the high viscosity, which develops when a finely divided layer silicate like bentonite is incorporated and hampers pumping of the system (sealing and filling masses with 80% bentonite are described), a granulated material with viscosity-breaking additives is used.

The difficulty that the swellable layer silicate can be prevented from swelling and forming the optimal Theological properties by the system in which it is to be incorporated can also occur similarly, if the system is not a cement-containing powder mixture, but also when the material is mixed into a surfactant solution. Normally, surfactant adsorption on the layer silicate surface suppresses swelling of the layer silicate, just like the presence of cations, e.g. Ca ions, etc.

The particle size of bentonites and the effect of this particle size on dispersibility in water are discussed in U.S. Pat. No. 2,036,617. It starts from the fact (page 1, column 2 and lines 43 ff.) that it was previously assumed that the bentonite particles are more readily dispersible, the finer they are. On the other hand, the inventors have found that, in certain cases, coarser bentonite particles are more readily dispersible than finer particles. The best effect is therefore assumed when the dried particles have roughly the same diameter and a certain preferred size. The smallest particle size lies at about 53 μm (250 mesh). In addition, according to this patent, only dispersal or dispersibility in water is at issue and not maintaining the highest effectiveness during use in powder systems, which can liberate polyvalent cations on contact with water.

DE-A-195 27 161 describes a pigment mixture and a paint with improved gravure suitability, containing a finely divided calcium carbonate and at least one finely divided swellable layer silicate and/or an acid-activated layer silicate. A distinction is not made between a swellable layer silicate and a swellable material, both of which are considered equivalent with respect to improvement of gravure printability. The mentioned pigment ($CaCO_3$ and swellable (or equivalent) acid layer silicate) have the usual unity for paper coating. An excessively high swelling capacity, however, is produced by coatings with unduly high viscosity, in which an acid-decomposed layer silicate is preferred during incorporation of a swellable layer silicate in a calcium carbonate dispersion. It cannot be gathered from the document that the layer silicate is supposed to be used for application in a medium that reduces swellability.

DE-A-44 38 305 concerns a pigment for coating of printing paper, especially a color developer pigment for carbon-less copying papers. The color development properties are achieved by acid activation of an alkali and/or alkaline earth smectite or by coating or activation with Lewis acids. The objective is to provide sufficiently reactive centers for color development without allowing the BET surface of the forming product to become too high, since otherwise too much binder is required for paper coating. The document contains no indications of special fineness of the material and the use of the material in a medium that reduces swellability.

DE-A-44 13 672 also concerns a color developer for carbon-less copying papers based on a swellable layer silicate, characterized by the fact that the amount of swellable layer silicate is 50 to 100 wt. %, and that the layer silicate has a swelling volume of 5 to 30 mL, referred to a suspension of 2 g in 100 mL water, and a specific surface area of >140 $m^2/g$. Deliberate further admixing of extender pigments, like silicates or inexpensive fillers, like kaolin or calcium carbonate, is mentioned; however, there is no indication of a particularly advantageous fineness. The color developers are also not used in a medium that reduces swellability.

DE-A-42 17 779 concerns a coating pigment for coating of print carriers, especially paper and cardboard, containing at least one swellable layer silicate that can be fixed essentially without binder onto the print carrier, in which the percentage of swellable layer silicate is at least 30 wt. % and the swelling volume of the coating pigment is 5 to 28 mL, referred to a suspension of 2 g coating pigment in 100 mL water. However, the document makes no mention of the behavior of the coating pigment in a medium that reduces swellability.

DD-A-219 170 concerns a method for activation of raw clays. It makes no mention that the material is to be used in a medium that reduces swellability.

DE-C 108 143 also concerns merely a method for preparation of highly swellable materials from clay minerals, in which activation is conducted in conjunction with alkali ions, especially Na ions with addition of magnesium salts.

CH-A-459 858 concerns an additive for mixtures based on cement and a method for its production. The additive is added to a mixture of cement and sand with a specific particle size distribution and contains at least one substance belonging to the montmorillonite group, at least one filler component with hydraulic properties and at least one stress reliever and at least one setting regulator. The substance belonging to the montmorillonite group is not further specified, except that it must be contained in a specific percentage. The preferred bentonite can also be replaced by an organophilic bentonite. The fineness of the entire additive mixture is 8 to 10 μm.

The underlying task of the invention is to furnish swellable layer silicates based on smectite for use in media that reduce swellability. These media include powdered mineral binder systems or other powdered and water-soluble salt-containing systems or surfactant solutions. This generally also includes all aqueous systems containing components that can hamper swelling. Even if the swellable layer silicates are not used as pre-swollen suspensions, they are supposed to simultaneously retain the potential effect fully or largely so. A special task was to furnish swellable layer silicates that produce stabilization and an increase in viscosity when incorporated in suspensions and/or solutions with di- or polyvalent cations (for example, suspensions and/or solutions of calcium hydroxide or slaked lime (like lime milk), calcium carbonate or similar calcium-rich compounds).

It was surprisingly found that a very fine division of layer silicates produces the desired effect. This is all the more so surprising, since one would expect that with a very finely divided layer silicate and with the increased exposed surface in the presence of Ca ions, which are also quickly dissolved in water, this surface would be occupied even more quickly by the divalent ions and swelling would therefore be suppressed more quickly and more effectively.

The object of the invention is therefore a swellable layer silicate based on smectite and/or sepiolite/palygorskite for use in media that reduce swellability and contain di- or polyvalent cations, characterized by a swelling volume of about 5 to 50 mL, measured by addition of 2 g of layer silicate to 100 mL of water, and by a fineness of a maximum of 5 wt. % >40 μm and preferably a maximum of 20% >20 μm as dry sieve residue.

The average particle diameter can also be determined, for example, in a laser measurement instrument (for example, Malvern). This should lie on the order of <15 μm, preferably <10 μm, especially <5 μm. In contrast to this, the particle fineness of commercial materials lies at a sieve residue of about 15% 45 μm or an average particle diameter of about 30 μm.

The fineness of materials introduced to hydraulically setting systems has already been partially described; however, mostly the usual product fineness of the offered powdered materials or special applications that do not concern the present invention are at issue.

A product that is used as a retarding agent for hydraulically setting systems and consists of about 30 to 60 wt. % of a lignosulfonate and/or polyphosphate and 60 to 30 wt. % of a mineral component (with limited surfactant addition) is described in EP-A-0 409 774. The mineral component (for example, vermiculite, bentonite, montmorillonite or perlite) should then have a residue of maximum 20% 50 μm.

A system is described in U.S. Pat. No. 5,588,990, in which very finely divided materials from talc and/or bentonite or equivalent materials, like fly ash, are added to a pozzuolana cement. A distinction is not made between the materials talc, (calcium) bentonite or fly ash. The effect of particle fineness on swelling capacity was not known.

An asbestos replacement system for cement systems is described in U.S. Pat. No. 5,637,144. The system consists of a combination of different materials, in which, among other things, a hydrophilic bentonite is mixed with a water retention agent and other additives. The finely divided material can also be a kaolin, montmorillonite, attapulgite, fuller's earth or kieselguhr. The essential property of the mineral is a certain water absorption capacity. The fineness of the materials, however, is not further defined.

The layer silicate according to the present invention is preferably present in a fineness of a maximum 10 wt. % >20 μm, maximum 5% >10 μm.

Layer silicate based on smectite or sepiolite/palygorskite is understood to mean a layer silicate from the smectite group and/or from the sepiolite/palygorskite group, including attapulgite and sepiolite.

The smectitic layer silicate is preferably chosen from the group bentonite, montmorillonite, hectorite, saponite, beidellite, sauconite of natural or synthetic origin or their mixtures, optionally with a percentage of layered extender silicates, like vermiculite, illite, mica, pyrophyllite, talc, kaolin. The content of montmorillonite in the smectitic layer silicate is preferably more than about 70 wt. %, especially more than about 80 wt. %, and, in particular, more than about 85 wt. %.

The layer silicate according to the invention can advantageously also contain an additive of a powdered alkali-containing substance.

The powdered alkali-containing substances include powdered water glasses, sequestering agents, like phosphates, zeolites or other materials that temporarily "immobilize" the soluble Ca ions of the binder system, like ion exchangers, and keep the layer silicate in swellable form long enough so that the lamellae are separated in water and swelling of the layer silicate can occur.

The object of the invention is also a method for production of the layer silicate according to the invention, characterized by alkaline activation of an alkaline earth layer silicate, drying and grinding of the material with superimposed screening. Alkaline activation of the alkaline earth layer silicate occurs in known fashion, for example, by treatment of a suspension of the layer silicate with soda.

Alkaline activation is also possible by mixing appropriate raw materials, like poorly swellable Ca-bentonite, with highly swellable Na-bentonite. The combination of swellable layer silicates of the smectite group with other not very swellable layer silicates of the, for example, sepiolite/polygorskite group, is also possible, in order to obtain the desired swelling volume. During activation in the normal case, the clay according to the invention is always subjected to a high-shear, high-energy mechanical process, in order to ensure that the intended ion exchange also occurs and the desired effect is recognizable in the system. Appropriate methods for activation are familiar to one skilled in the art and include edge mills (pan grinders), extruder methods, roll stands, colloid mills, etc. The optimal method is guided according to the available raw material, which requires relatively little shear energy, depending on the moisture content and plasticity, or can make repeated processing with high-energy input necessary. This can be determined by one skilled in the art by means of routine experiments. This can be done by suspending the clay in water and subjecting it in readily pumpable form to colloid mill treatment, for example, treatment with a Manton-Gaulin mill or microfluidizer treatment, in which two suspension streams are forced against each other under high pressure in the fashion of a jet mill and the desired shear energy is introduced by this. In the case of activation in the "suspended state" and the presence of a readily pumpable suspension, the clay can naturally also be purified and produced via ordinary drying and grinding methods.

One variant of the method according to the invention is characterized by alkaline activation of an alkaline earth layer silicate suspended in an aqueous medium, removal of the coarse additives and spray-drying of the dilute suspension, and optionally by grinding and screening of the spray-dried particles, if these have still not reached the aforementioned particle fineness.

The coarse additives include quartz, feldspar and mica particles, which are ordinarily removed by passing a suspension of the alkaline earth layer silicate through a hydrocyclone.

Another object of the invention is a mineral binder system, especially a dry mortar system, containing a swellable layer silicate. Mineral binder systems include construction material mixtures, like mortar, flooring plasters, plasters and construction glues.

The object of the invention is also the use of the swellable layer silicate according to the invention in media that reduce swelling capability. The swellable layer silicate according to the invention can then be part of the powder mixture or added separately in powdered or pre-dispersed form to the medium under the influence of shear forces.

A special application consists of controlling the rheology and/or stability of the powdered and/or liquid media with a content of electrolytes and/or surfactants.

The electrolytes are ordinary soluble compounds of di- or polyvalent metals or mixtures of soluble and insoluble compounds of di- or polyvalent metals, like calcium carbonate and calcium hydroxide.

A special application lies in controlling the rheology and stability of the powdered mineral binder system, like systems based on hydraulically curing binders, in which the layer silicate is either a component of the powder mixture or is mixed with the powdered mineral binder systems from an aqueous suspension using shear forces.

Slumping of a plaster on the wall can also be prevented by using the layer silicate according to the invention and the non-sag properties therefore increased.

Another special application lies in controlling the rheology and stability of suspensions and/or solutions with di- or polyvalent cations (for example, suspensions and/or solutions of calcium hydroxide (like lime milk), calcium carbonate or similar calcium-rich compounds).

Another advantage according to the invention consists of preventing or reducing syneresis, especially under transport conditions, as well as an improvement in (re)mixability in the aforementioned systems and media, which can only otherwise be achieved by organic wetting agents.

The swelling volume was measured as follows: A graduated 100 mL cylinder is filled with 100 mL distilled water, 2 g (air-dried) of the layer silicate being measured is slowly introduced batchwise (about 0.1 to 0.2 g) to the surface of the water with a spatula. One waits for settling of the added batch before the next batch is added. After 2 g is added and has settled to the bottom of the graduated cylinder, the height that the swollen substance occupies in the graduated cylinder in mm/2 g is interpreted after one hour.

The layer silicates according to the invention are further explained in non-restrictive fashion in the following examples.

EXAMPLE 1

A commercially available Ca-bentonite activated with soda (commercial product Tixoton® CV 15 from Süd Chemie AG) (sample A) is used. The following particle size distribution is obtained for this material from laser (Malvern) powder analysis:

Residue at 20 μm: 60%
Residue at 40 μm: 40.8%

The average particle diameter is therefore about 30 μm. Part of this material is then subjected to further grinding (sample C). Particle size distribution of this material (measured in the same laser apparatus) is:

Residue at 20 μm: 10.53%
Residue at 40 μm: 0.38%

The average particle diameter is about 4.5 μm.

The swelling volume of sample C is 36 mL. The swelling volume was measured as indicated above:

Experiment 1a):

Both samples (A and C) are initially dispersed in water and the viscosity of the 8% suspension is measured in a Brookfield rheometer. Test method: 92 g tap water is introduced to a 250 mL beaker. 8 g bentonite (air-dried) is added over 60 seconds during agitation in a laboratory dissolver (940 rpm). It is then further agitated at 2800 rpm for 10 minutes. The viscosity is measured after 1 hour of swelling time on the rheometer (Brookfield). The obtained results are shown in Table I:

TABLE I

| Sample A | Sample A | Sample C | Sample C |
| --- | --- | --- | --- |
| Brookfield 10 rpm Pa · s 2200 | Brookfield 100 rpm Pa · s 310 | Brookfield 10 rpm Pa · s 2120 | Brookfield 100 rpm Pa · s 275 |

In the test system water alone, no distinction can be found between the thickening effect of the standard material (A) and the further ground sample (C).

Experiment 1b):

If the yield point is measured according to Soos with the "ball-wire screen" (yield point in $N/m^2$ in a 6% suspension according to DIN 4126), surprisingly distinct differences are found.

The following measurement method was used:

2 liters of tap water is introduced to a 5 liter vessel. 120 g layer silicate is stirred in with a laboratory dissolver at 940 rpm over 60 seconds. It is then agitated for another 5 minutes at 2800 rpm. The suspension is then introduced to a closeable container. After 1 hour and 24 hours of swelling time, 1 liter of the suspension is filled into a plastic container and agitated briefly by hand. After 1 minute of standing, the test balls are immersed into the suspension by means of the ball-wire screen device. The first sagging ball is decisive for the yield point (DIN 4126, Appendix B).

The results are shown in Table II

TABLE II

| Sample A | Sample A | Sample C | Sample C |
| --- | --- | --- | --- |
| Yield point after 1 h Ball no. 4 18.1 $N/m^2$ | Yield point after 24 h Ball No. 6 35.9 $N/m^2$ | Yield point after 1 h Ball no. 5 25.2 $N/m^2$ | Yield point after 24 h Ball no. 8 49.9 $N/m^2$ |

The buildup of a yield point occurs with the further ground samples see more quickly and gives higher values. This property of the yield point is invariably of significance if either heavy components of a flowable aqueous system are to be prevented on setting (filling concrete) or the no-sag time (for example, of a base plaster on a wall) is to be lengthened.

EXAMPLE 2

The experiment on yield point determination of example 1b is repeated, but now a mixture of 95 parts by weight layer silicate and 5 parts by weight cement (CEM II/A-L 32.5 R) is used, instead of the layer silicate. The yield point is determined in a Bohlin rheometer CS 50: Sample B is a standard material (A) with 5 wt. % cement; Sample D corresponds to Sample C with 5% cement. It is apparent from Table II that in the presence of cement, the fine sample D (from C) produces a much better effect.

TABLE III

| Sample B | Sample B | Sample D | Sample D |
| --- | --- | --- | --- |
| Yield point after 1 h 27.6 Pa · s | Yield point after 24 h 67.6 Pa · s | Yield point after 1 h 42.5 Pa · s | Yield point after 24 h 113.0 Pa · s |

EXAMPLE 3

The experiment of example 2 is repeated with a mixture of cement: Layer silicate=85:15. The dry mixture is prepared with tap water in a weight ratio 1:1. 100 g water is introduced to a beaker and 100 g of the mixtures are added over 120 seconds during agitation in a laboratory dissolver at 940 rpm. It is then agitated for another 5 minutes at 2800 rpm. The samples are then measured after a swelling time of 15 minutes and 30 minutes in a Bohlin rheometer. Before each measurement, the sample is carefully agitated with the spatula. Sample E=15 parts by weight sample A+85 parts by weight cement; sample F=15 parts by weight sample C+85 parts by weight cement; the results are shown in Table IV:

TABLE IV

| Sample E | Sample E | Sample F | Sample F |
| --- | --- | --- | --- |
| Yield point after 15 minutes 9.22 Pa · s | Yield point after 30 minutes 7.58 Pa · s | Yield point after 15 minutes 10.9 Pa · s | Yield point after 30 minutes 12.6 Pa · s |

Despite the high cement fraction, it is again readily apparent here that the material according to the invention is more effective and builds up higher yield points. This yield point is also stable in the sample (F) according to the invention and even is improved somewhat, indicating final swelling, whereas the standard material (E) already flocculates and shows degradation of the yield point.

EXAMPLE 4

In this example, the effect of fineness on dispersibility of the employed materials is tested in an already available cement suspension. An available cement suspension (50 g cement in 50 g water) is agitated into 4 g of sample A and C each over 60 seconds (940 rpm) and then further agitated for 5 minutes (1865 rpm). Measurement of the samples again occurs in a Bohlin rheometer after a swelling time of 15 and 30 minutes.

Sample G=4 g sample A in 100 g cement+water,
Sample H=4 g sample C in 100 g cement+water.
The results are shown in Table V.

TABLE V

| Sample G | Sample G | Sample H | Sample H |
| --- | --- | --- | --- |
| Yield point after 15 minutes | Yield point after 30 minutes | Yield point after 15 minutes | Yield point after 30 minutes |
| 10.9 Pa · s | 10.9 Pa · s | 12.5 Pa · s | 12.6 Pa · s |

The materials according to the invention are also superior in this system (4% layer silicate, referred to cement) to the standard material.

EXAMPLE 5

The effect/reduction of rebound fraction of a shotcrete was investigated.

The rebound fraction is dependent on the shotcrete consistency on the application surface. This is influenced by the particle structure of the fine and coarse additive, as well as the amount and flowability of the cement paste. The concrete occurring on the application surface should be as plastic as possible, so that the occurring added grains can be well embedded. However, the intrinsic weight must not be greater than the tensile capability (internal cohesion) of the shotcrete and the adhesive pull strength at the shotcrete/substrate interface or even the tensile strength of the interface. Both insufficient adhesion capacity and internal cohesion would otherwise result in rebound. A thixotropic flow behavior with rapid buildup of a pronounced yield point is therefore sought. The following was used as very fine mortar:

Dry mortar: 500 g CEM 1 42.5 R+150 g quartz sand 0/0.5+ powdered layer silicate
Mixing water: 250 g total water+liquid layer silicate The corresponding metering amounts of sample C were added to the cement samples by means of a blunger and homogenized for about 2 minutes. As a result of the different metered amounts, the water demand also varied, so that during spraying, after the spray experiments with constant W/C (water/cement) value, attention was focused on the identical consistency of the shotcrete.

In these experiments, the additive "Eberstein" (Dolomite Eberstein Neuper GmbH) GK 4 mm; particle size distribution curve (A+B)/2; 3% intrinsic moisture) and the spray binder (Chronolith® ST, Heidelberger Zement) were emptied separately into the feed hopper of two screw metering devices. Metering of the binder occurred directly before the beginning of spraying with calibrated screws that were set so that a binder content of 380 kg/m³ was produced. The mixing ratio of binder/additive was 1:4.88 and was kept constant for the entire series of experiments. Water addition (pressure: 7 bar) occurred at the nozzle, which could be precisely maintained by the nozzle operator by continuous observation of the water flow meter at the pre-established W/C value. The spray nozzle spacing to the application surface and all experiments was 0.8 to 1.0 m.

To record the rebound fraction during application of the shotcrete into wooden boxes (30×40×10 cm; shotcrete layer thickness=about 10 cm), the rebound was trapped by a tarpaulin spread out on the floor and weighed. The weight of the shotcrete was obtained from difference weighing, weight of the shotcrete+boarding−the weight of the boarding. Consequently, the rebound is calculated in percent:

$$\text{Rebound}: \frac{Weight_{rebound}}{Weight_{shotcrete} + Weight_{rebound}} \times 100(\%)$$

The results are shown in Table VI

TABLE VI

| Layer silicate | Metering (wt. % of cement content) | Rebound value (%) | W/C value |
| --- | --- | --- | --- |
| C | 0.0 | 30.2 | 0.47 |
| C | 1.0 | 23.8 | 0.47 |
| C | 1.6 | 22.8 | 0.47 |
| C | 2.0 | 27.8 | 0.47 |
| C | 1.0 | 21.6 | 0.48 |
| C | 1.6 | 14.8 | 0.51 |
| C | 2.0 | 15.4 | 0.52 |
| C | 0.0 | 25.1 | 0.51 |
| A | 1.0 | 25.2 | 0.46 |
| A | 2.0 | 30.4 | 0.44 |
| A | 2.0 | 22.3 | 0.53 |

Addition of the powdered layer silicate according to the invention therefore exhibits good reduction of rebound fraction, which can only be explained by rapid formation of a house-of-cards structure, i.e., by yield point/thixotropy achieved by delamination. The standard comparison material A also shows a certain effect, but this is much poorer than with the material according to the invention.

EXAMPLE 6

Ca-bentonite activated with soda (Tixoton®—product of Süd-Chemie AG similar to example 1) was used with different fineness and workup:

Sample A, standard bentonite: Fineness from 20% >45 µm
Sample B, bentonite with the finest grinding: Fineness of 3% >45 µm
Sample C, bentonite with the finest grinding and purification by screening: Fineness of 1% >45 µm Experiment 6a)

Samples A, B and C were first dispersed in water and the viscosity of the 5% suspension measured with a Brookfield viscosimeter.

Test method: 190 g tap water was introduced to a 600 mL beaker. 10 g bentonite (air-dried) was added over 6 seconds during agitation with a laboratory dissolver (930 rpm). It is then agitated for 15 minutes at 2800 rpm. Measurement of the viscosity occurs after 1 day of swelling time on the viscosimeter (Brookfield). The obtained results are shown in Table VII.

TABLE VII

|  | Viscosity, Brookfield 10 rpm (mPa s) |
|---|---|
| Sample A | 3300 |
| Sample B | 3780 |
| Sample C | 4500 |

Experiment 6) (30% $Ca(OH)_2$ Suspension

| Formula: | 50 parts by weight bentonite suspension, 5% |
|---|---|
|  | 20 parts water |
|  | 30 parts slaked lime powder ($Ca(OH)_2$) |

150 g bentonite suspension from experiment 6a is introduced to a 600 mL beaker and mixed with 60 g of water. For homogenization, it is agitated for 15 seconds with laboratory dissolver. In a null sample without bentonite, 210 g of water is introduced instead. 90 g slaked lime powder is then added batchwise, with the dissolver running, over 5 minutes. The agitator speed is increased in steps and finally amounts to 2800 rpm. Partial samples of 100 mL are filled into a 100 mL graduated glass cylinder (diameter 3 cm). The remaining samples are filled into plastic containers.

After 1 week of standing, the clear liquid separation (syneresis) at the top of the graduated cylinder is interpreted and the viscosity (Brookfield) measured in the samples stored in the plastic containers.

It is apparent from Table VIII that ordinary bentonite products (A), despite a certain thickening effect, produce almost no stabilizing effect for the $Ca(OH)_2$ suspension. With the same amounts (2.5%) of finer bentonite (B and C), on the other hand, the syneresis is significantly reduced.

TABLE VIII

|  | Syneresis after 1 week | Viscosity, Brookfield 10 rpm (mPa · s) |
|---|---|---|
| Null sample | 15% | 1520 |
| Sample A | 12% | 3020 |
| Sample B | 8% | 3740 |
| Sample C | 3.5% | 4280 |

EXAMPLE 7

The experiment of example 6 is repeated, but the concentration of the $Ca(OH)_2$ suspension being stabilized is 40%. Corresponding to the lower water content and the higher base viscosity, less bentonite is used for stabilization, namely, 0.75% (corresponding to 15% of the 5% bentonite suspension from experiment 6a).

| Formula: | 45 g (15%) bentonite suspension, 5% |
|---|---|
|  | 135 g (45%) water |
|  | 120 g (40%) slaked lime powder ($Ca(OH)_2$) |

The test method is similar to experiment 6b, in which 180 g of water is introduced to the null sample. The results in Table IX also demonstrate the superior stabilization effect of the finer bentonites (B and C).

TABLE IX

|  | Syneresis after 1 week | Viscosity, Brookfield 10 rpm (mPa · s) |
|---|---|---|
| Null sample | 3.5% | 3640 |
| Sample A | 3% | 4160 |
| Sample B | 2% | 4340 |
| Sample C | 1% | 5320 |

EXAMPLE 8

The experiment from example 7 is repeated, in which the charge size is 2 kg, instead of 300 g. The samples are filled into closed plastic containers and transported in a vehicle 100 km (parts of city traffic, country roads, freeway). Under these transport conditions, the liquid separation (syneresis) is generally higher than during standing storage in glass cylinders.

Measurement occurs here by pouring out and weighing the clear liquid. After repouring, the agitatability of the sedimented suspension is qualitatively evaluated.

The results in Table X show that fine bentonite, in comparison with standard bentonites, not only reduce the syneresis under transport conditions, but also improve subsequent agitatability.

TABLE X

|  | Syneresis after 100 km vehicle transport | Agitatability |
|---|---|---|
| Null sample | 15% | very poor |
| Sample A | 14% | poor |
| Sample B | 8% | good |
| Sample C | 5% | very good |

The invention claimed is:

1. A material for use in media containing di- or polyvalent cations that reduce swellability, comprising a swellable layer silicate selected from a smectite or a sepiolite/palygorskite clay group, wherein the selected swellable layer silicate has a swelling volume of about 5 to 50 mL, when measured by addition of 2 g of the layer silicate that has been air-dried to 100 mL water, and a fineness, wherein no more than about 5 wt. % of the layer silicate has a particle size greater than about 40 µm and wherein no more than 20 wt. % of the layer silicate has a particle size greater than about 20 µm, when measured as a dry sieve residue.

2. The material of claim 1, wherein no more than about 10 wt. % of layer silicate has a particle size greater than about 20 µm.

3. The material of claim 1, wherein no more than about 5 wt. % of layer silicate has a particle size greater than about 10 µm.

4. The material of claim 1, wherein the swelling volume of the selected layer silicate is from about 10 to 40 mL, when measured by addition of 2 g of the layer silicate to 100 mL water.

5. The material of claim 1, wherein the swelling volume of the layer silicate is from about 20 to 35 mL, when measured by addition of 2 g of the layer silicate to 100 mL water.

6. The material of claim 1, wherein the smectite or sepiolite/palygorskite clay is selected from bentonite, montmorillonite, hectorite, attapulgite or palygorskite, saponite, beidellite, sauconite, or mixtures thereof of natural or synthetic origin.

7. The material of claim 1 further comprising a layered extender silicate selected from the group consisting of vermiculite, illite, mica, pyrophyllite, talc, and kaolin.

8. The material of claim wherein the swellable layer silicate comprises at least about 70 wt. % montmorillonite.

9. The material of claim 1 wherein the swellable layer silicate comprises at least about 80 wt. % montmorillonite.

10. e material of claim 1 wherein the swellable layer silicate comprises at least about 85 wt. % montmorillonite.

11. The material of claim 1 further comprising a powdered alkali-containing substance.

12. A mineral binder system, comprising a dry mortar system, comprising the swellable layer silicate of claim 1.

13. The mineral binder system of claim 12, wherein the swellable layer silicate comprises about 0.1 to 5 wt. %, of the total system.

* * * * *